(12) United States Patent
Morino et al.

(10) Patent No.: US 6,635,665 B2
(45) Date of Patent: Oct. 21, 2003

(54) REMEDIES OR PREVENTIVES FOR PULMONARY INSUFFICIENCY CONTAINING DIAMINOTRIFLUOROMETHYLPYRIDINE DERIVATIVES

(75) Inventors: Kyuya Morino, Shiga (JP); Shuichi Yotsuya, Shiga (JP); Masashi Imamura, Shiga (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 10/181,431

(22) PCT Filed: Jan. 30, 2001

(86) PCT No.: PCT/JP01/00616

§ 371 (c)(1),
(2), (4) Date: Jul. 25, 2002

(87) PCT Pub. No.: WO01/56570

PCT Pub. Date: Aug. 9, 2001

(65) Prior Publication Data

US 2003/0109551 A1 Jun. 12, 2003

(30) Foreign Application Priority Data

Feb. 1, 2000 (JP) ......................................... 2000-024349

(51) Int. Cl.$^7$ ........................ A61K 31/44; C07D 213/75
(52) U.S. Cl. ........................................ 514/352; 546/308
(58) Field of Search ........................... 514/352; 546/308

(56) References Cited

U.S. PATENT DOCUMENTS

| 5,229,403 A | 7/1993 | Haga et al. ................. 514/352 |
| 5,492,908 A | 2/1996 | Haga et al. ............... 514/222.2 |
| 6,197,796 B1 | 3/2001 | Ogura ........................ 514/352 |

OTHER PUBLICATIONS

L. Touqui et al.: "A role for pholpholipase A2 in ARDS pathogenesis" Mol. Med. Today, vol. 3, pp. 244–249 1999.
D.L. Bowton et al.: "Phospholipase A2 and arachidonate increase in bronchoalveolar lavage fluid after inhaled antigen challengein athmatics" Am. J Rtesip. Crit. Care Med., vol. 155, pp. 421–425 1997.
L. Arbibe et al.: "Generation of lyso–phospholipids from surfactant in acute injury is mediated by type–II phospholipase A2 and inhibited by direct surfactant protein A–phospholipase A2 protein interaction" J. Clin. Invest., vol. 102, No. 6, pp. 1152–1160 1998.

Primary Examiner—Zinna Northington Davis
(74) Attorney, Agent, or Firm—Oblon, Spivak, McClelland, Maier & Neustadt, P.C.

(57) ABSTRACT

A therapeutic or preventive agent for pulmonary insufficiency, containing as an active ingredient a diaminotrifluoromethylpyridine derivative represented by the formula (I) or its salt:

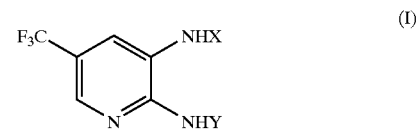

wherein X is a —$CW^1R^1$ group, a —$COCOR^2$ group, a —$CW^1NHCOR^2$ group, a —$C(=W^1)W^2R^3$ group or a —$CW^1N(R^4)R^5$ group; Y is an alkyl group, a —$CW^3R^6$ group, a —$COCOR^7$ group, a —$NHCOR^7$ group, a —$C(=W^3)W^4R^8$ group, a —$(NH)_mSO_2R^9$ group, a —$(NH)_mSO_2OR^{10}$ group or a —$(NH)_mSO_2N(R^{11})R^{12}$ group; each of $R^1$, $R^6$ and $R^9$ is a chain hydrocarbon group, a monocyclic hydrocarbon group, a polycyclic hydrocarbon group, a monocyclic heterocycle group or a polycyclic heterocycle group; each of $R^2$ and $R^7$ is an alkyl group, an alkoxy group, a phenyl group or a phenoxy group; each of $R^3$, $R^8$ and $R^{10}$ is an alkyl group, an alkenyl group, an alkynyl group, a cycloalkyl group, a phenyl group or a benzyl group; each of $R^4$, $R^5$, $R^{11}$ and $R^{12}$ is an alkyl group; each of $W^1$, $W^2$, $W^3$ and $W^4$ is an oxygen atom or a sulfur atom; and m is 0 or 1, is provided.

23 Claims, No Drawings

REMEDIES OR PREVENTIVES FOR PULMONARY INSUFFICIENCY CONTAINING DIAMINOTRIFLUOROMETHYLPYRIDINE DERIVATIVES

CROSS REFERENCE TO RELATED CASES

The present application is a 371 application of PCT/JP01/00616, filed on Jan. 30, 2001, which claims priority to Japanese Application No. JP 2000-24349, filed on Feb. 1, 2000, which are hereby incorporated by reference in their entirety.

TECHNICAL FIELD

The present invention relates to a therapeutic or preventive agent for pulmonary insufficiency containing as an active ingredient a diaminotrifluoromethylpyridine derivative or its salt.

BACKGROUND ART

Japanese Patent No. 2762323 and U.S. Pat. No. 5,229,403 disclose that a diaminotrifluoromethylpyridine derivative or its salt has a phospholipase $A_2$ inhibitory action and is useful as an active ingredient of an anti-inflammatory agent or an anti-pancreatitis agent. They also disclose that (1) phospholipase $A_2$ is secreted or activated in platlets or inflammatory cells by stimulations and contributes to the production of a platlet activating factor (PAF) and arachidonic acid metabolites, (2) the arachidonic acid metabolites are closely related to various diseases, for example, inflammatory symptoms such as rheumatic arthritis, arthritis deformans, tendinitis, bursitis, psoriasis and related dermatitis; nasal and bronchial airway troubles such as allergic rhinitis and allergic bronchial asthma; and immediate hypersensitive reactions such as allergic conjunctivitis, (3) on the other hand, phospholipase $A_2$ secreted from pancreas is activated in the intestine and exhibits a digestive action, but once activated in the pancreas, it is believed to be one of the factors causing pancreatitis, and (4) the above diaminotrifluoromethylpyridine derivative inhibits phospholipase $A_2$ and thus is effective for treatment of diseases related to phospholipase $A_2$ such as inflammatory symptoms, nasal and bronchial airway troubles, immediate hypersensitive reactions or pancreatitis, and can be used as an anti-inflammatory agent, an agent for treating bronchial asthma, an anti-allergy agent, an anti-pancreatitis agent, an anti-nephritis agent or an anti-multiple organ failure agent.

Further, U.S. Pat. No. 5,492,908 discloses that such compounds can be used as a therapeutic agent for rheumatoid arthritis, and JP-A-10-298076 discloses that some of these compounds are effective as an anticancer agent having a carcinogenesis inhibitory effect.

Among pulmonary insufficiencies, as intractable and particularly problematic diseases, acute respiratory distress syndrome (ARDS) and chronic obstructive pulmonary disease (COPD) may be mentioned.

ARDS occurs when excessive invasion due to various underlying diseases is applied to the body. The underlying diseases may, for example, be viral pneumonia, bacterial pneumonia, infection, bacteraemia, systemic inflammatory response syndrome (SIRS), sepsis, severe sepsis, septic shock, haemorrhagic shock, cardiogenic shock, anaphylaxis, hypotension, multiple organ failure (MOF), multiple organ dysfunction syndrome (MODS), acute pancreatitis, disseminated intravascular coagulopathy (DIC), direct pulmonary contusion, head injury, multiple severe injury, fat embolism, amniotic embolism, fetal death, oxygen intoxication, drug intoxication, massive deglutition in stomach, drowning and high altitude pulmonary edema. On ARDS patients, usually an acute respiratory failure symptom such as non-cardiogenic pulmonary edema, severe hypoxemia, decrease in pulmonary compliance, severely impaired gas exchange or dyspnea is observed. However, it tends to be difficult to treat ARDS with general oxygen therapy, and treatment by an artificial ventilation method employing positive end-expiratory pressure (PEEP) or pressure cycled artificial ventilation is carried out in many cases. Further, it is attempted to carry out extracorporeal pulmonary assist or nitrogen monooxide inhalation therapy in some cases.

As a drug treatment for ARDS, drugs such as various steroids such as prednisolone, proteinase inhibitors such as ulinastatin, prostaglandin E1, pulmonary surfactant, pentoxifylline and granulocyte colony stimulating factor have clinically been applied, but, because, the underlying diseases for ARDS are various as described above, their effectiveness has not clearly been understood. Further, the mortality rate by ARDS is so high as about 50%. It has been known that human derived anti-thrombin III is useful as a therapeutic agent for ARDS and that a medical composition for bronchoalveolar lavage comprising a surfactant containing polypeptides is effective for treatment of ARDS, however, development of safer and more effective therapeutic or preventive agents containing a low molecular weight compound as an active ingredient has been desired.

On the other hand, COPD is a general term for pulmonary diseases which cause delayed forced expiratory flow, including chronic bronchitis, emphysema, diffuse panbronchiolitis and airway obstruction symptom. Smoking and aging are main causes of crises, and the incidence rate of moist cough and other respiratory symptoms is high particularly among long-term heavy smokers, and their mortality rate also tends to be high. Further, along with progress of environmental pollution in recent years, exposure to powder dust and chemical fume in the air tends to increase, whereby the incidence rate of COPD tends to increase, and the number of patients is rapidly increasing year by year. At the initial stage of COPD, acute pathologic symptoms in the chest characterized by increase of cough, pyogenic expectoration, wheezing and dyspnea, and pyrexia on occasion, are confirmed. Many of them are progressive, tend to worsen successively with repetition of acute exacerbation, and may cause severe hypoxemia accompanied by cyanosis or may cause disease complication such as acute respiratory failure, severe pneumonia, pneumothorax or pulmonary embolism, thus causing the patient to die in some cases.

The accurate cause of crisis of COPD has not been understood, and thus no radical treatment has been developed yet. For its treatment, long term oxygen therapy may be carried out in some cases. Further, as symptomatic drug treatment, a $\beta_2$ agonist such as metaproterenol which accelerates bronchodilation or theophylline which decreases convulsion of the smooth muscle may, for example, be used with a purpose of reducing airway obstruction. Further, anticholinergic agonists, steroid drugs and antibacterial agents may also be used alone or as multiple drug combination, however, if systemic application of a steroid drug is required, its adverse reactions are problematic, and accordingly development of safe and more effective therapeutic agents has been desired.

DISCLOSURE OF THE INVENTION

The present inventors have conducted extensive studies on pharmacological effects of diaminotrifluoromethylpyridine derivatives or their salts and as a result, found that these compounds are extremely effective as a therapeutic or preventive agent for pulmonary insufficiency represented by ARDS or COPD, and the present invention has been accomplished on the basis of this discovery.

The present invention provides a therapeutic or preventive agent for pulmonary insufficiency, containing as an active ingredient a diaminotrifluoromethylpyridine derivative represented by the formula (I) or its salt:

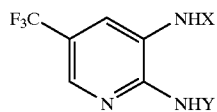

(I)

wherein X is a —$CW^1R^1$ group, a —$COCOR^2$ group, a —$CW^1NHCOR^2$ group, a —$C(=W^1)W^2R^3$ group or a —$CW^1N(R^4)R^5$ group; Y is an alkyl group, a —$CW^3R^6$ group, a —$COCOR^7$ group, a —$NHCOR^7$ group, a —$C(=W^3)W^4R^8$ group, a —$(NH)_mSO_2R^9$ group, a —$(NH)_mSO_2OR^{10}$ group or a —$(NH)_mSO_2N(R^{11})R^{12}$ group; each of $R^1$, $R^6$ and $R^9$ which are independent of one another, is a chain hydrocarbon group which may be substituted, a monocyclic hydrocarbon group which may be substituted, a polycyclic hydrocarbon group which may be substituted, a monocyclic heterocycle group which may be substituted or a polycyclic heterocycle group which may be substituted; each of $R^2$ and $R^7$ which are independent of each other, is an alkyl group which may be substituted, an alkoxy group which may be substituted, a phenyl group which may be substituted or a phenoxy group which may be substituted; each of $R^3$, $R^8$ and $R^{10}$ which are independent of one another, is an alkyl group which may be substituted, an alkenyl group which may be substituted, an alkynyl group which may be substituted, a cycloalkyl group which may be substituted, a phenyl group which may be substituted or a benzyl group which may be substituted; each of $R^4$, $R^5$, $R^{11}$ and $R^{12}$ which are independent of one another, is an alkyl group which may be substituted; each of $W^1$, $W^2$, $W^3$ and $W^4$ which are independent of one another, is an oxygen atom or a sulfur atom; and m is 0 or 1, excluding a case where one of X and Y is a —$COCF_2X^1$ group (wherein $X^1$ is a hydrogen atom, a halogen atom, an alkyl group or a haloalkyl group), and the other is a —$COCF_2X^2$ group (wherein $X^2$ is a hydrogen atom, a halogen atom, an alkyl group, a haloalkyl group or an alkylcarbonyl group), a —$COOX^3$ group (wherein $X^3$ is an alkyl group which may be substituted or a phenyl group which may be substituted) or a —$COX^4$ group (wherein $X^4$ is an alkyl group, a haloalkyl group, an alkenyl group, an alkynyl group, a phenyl group which may be substituted, a furanyl group or a naphthyl group).

In the formula (I), the above chain hydrocarbon group for each of $R^1$, $R^6$ and $R^9$ may, for example, be an alkyl group, an alkenyl group or an alkynyl group. The above monocyclic hydrocarbon group may, for example, be a cycloalkyl group, a cycloalkenyl group or a phenyl group. The polycyclic hydrocarbon group may be a condensed polycyclic hydrocarbon group such as a naphthyl group, a tetrahydronaphthyl group or an indanyl group, or a bridged polycyclic hydrocarbon group such as an adamantyl group, a noradamantyl group, a norbornanyl group or a norbornanonyl group. The above monocyclic heterocycle group may, for example, be a pyrrolyl group, a furanyl group, a thienyl group, a pyrazolyl group, an imidazolyl group, an oxazolyl group, an isoxazolyl group, a thiazolyl group, an isothiazolyl group, a thiadiazolyl group, a pyrrolinyl group, a pyrrolidinyl group, a dihydrofuranyl group, a tetrahydrofuranyl group, a dihydrothienyl group, a tetrahydrothienyl group, a pyrazolinyl group, a hydantoinyl group, an oxazolinyl group, an isoxazolinyl group, an isoxazolidinyl group, a thiazolinyl group, a thiazolidinyl group, a dioxolanyl group, a dithiolanyl group, a pyridyl group, a pyridazinyl group, a pyrimidinyl group, a pyrazinyl group, a dihydropyridyl group, a tetrahydropyridyl group, a piperidinyl group, a dihydrooxopyridazinyl group, a tetrahydrooxopyridazinyl group, a dihydrooxopyrimidinyl group, a tetrahydrooxopyrimidinyl group, a piperazinyl group, a dihydropyranyl group, a tetrahydropyranyl group, a dioxanyl group, a dihydrodithinyl group, a dithianyl group or a morphorinyl group. The above polycyclic heterocycle group may be a condensed polycyclic heterocycle group such as a thienothienyl group, a dihydrocyclopentathienyl group, an indolyl group, a benzofuranyl group, a benzothienyl group, a benzoxazolyl group, a benzisoxazolyl group, a benzothiazolyl group, a benzimidazolyl group, a tetrahydrobenzothienyl group, a dihydrobenzofuranyl group, a tetrahydrobenzisoxazolyl group, a benzodioxolyl group, a quinolinyl group, an isoquinolinyl group, a benzodioxanyl group or a quinoxalinyl group, or a bridged polycyclic heterocycle group such as a quinuclidinyl group.

The substituent for each of the chain hydrocarbon group which may be substituted for each of $R^1$, $R^6$ and $R^9$, the alkyl group which may be substituted and the alkoxy group which may be substituted for each of $R^2$ and $R^7$, the alkyl group which may be substituted, the alkenyl group which may be substituted and the alkynyl group which may be substituted for each of $R^3$, $R^8$ and $R^{10}$, the alkyl group which may be substituted for each of $R^4$, $R^5$, $R^{11}$ and $R^{12}$, and the alkyl group which may be substituted for $X^3$, may, for example, be a halogen atom, an alkoxy group, a haloalkoxy group, an alkylthio group, a cycloalkyl group, a cycloalkoxy group, a cycloalkenyl group, a cycloalkenyloxy group, an alkoxycarbonyl group, an alkylcarbonyl group, an alkylcarbonyloxy group, an aryl group, an aryloxy group, an arylthio group, an amino group or an amino group substituted with an alkyl group. The number of such substituents or substituents on such substituents may be one or more, and when the number is two or more, such substituents may be the same or different.

Further, the substituent for each of the monocyclic hydrocarbon group which may be substituted, the polycyclic hydrocarbon group which may be substituted, the monocyclic heterocycle group which may be substituted and the polycyclic heterocycle group which may be substituted for each of $R^1$, $R^6$ and $R^9$, the phenyl group which may be substituted and the phenoxy group which may be substituted for each of $R^2$ and $R^7$, the cycloalkyl group which may be substituted, the phenyl group which may be substituted and the benzyl group which may be substituted for each of $R^3$, $R^8$ and $R^{10}$, and the phenyl group which may be substituted for $X^3$, may, for example, be a halogen atom, an alkyl group, a haloalkyl group, an alkoxy group, a haloalkoxy group, an alkylthio group, a cycloalkyl group, a cycloalkoxy group, a cycloalkenyl group, a cycloalkenyloxy group, an alkoxycarbonyl group, an alkylcarbonyl group, an alkylcarbonyloxy group, an aryl group, an aryloxy group, an arylthio group, an amino group, an amino group substituted with an alkyl group, a cyano group or a nitro group. The number of such substituents or substituents on such substituents may be one or more, and when the number is two or more, such substituents may be the same or different.

In the formula (I), the alkyl group and the alkyl moiety contained in each of X and Y may, for example, be $C_{1-18}$ alkyl such as a methyl group, an ethyl group, a propyl group, a butyl group, a pentyl group, a hexyl group, a heptyl group, an octyl group, a decyl group or a nonadecyl group, and they include linear or branched aliphatic structural isomers. The alkenyl group and the alkenyl moiety contained in each of X and Y may be $C_{2-18}$ alkenyl such as a vinyl group, a propenyl group, a butenyl group, a pentenyl group, a hexenyl group, a decenyl group or a nonadecenyl group, and they include linear or branched aliphatic structural isomers. The alkynyl group and the alkynyl moiety contained in each of X and Y may be $C_{2-18}$ alkynyl such as an ethynyl group, a propynyl group, a butynyl group, a pentynyl group, a hexynyl group, a decynyl group or a nonadecynyl group, and they include linear or branched aliphatic structural isomers. The cycloalkyl group and the cycloalkyl moiety contained in each of X and Y may be $C_{3-8}$ cycloalkyl such as a cyclopropyl group, a cyclobutyl group, a cyclopentyl group, a cyclohexyl group or a cyclooctyl group. The cycloalkenyl group and the cycloalkenylmoiety contained in each of X and Y may be $C_{5-8}$ cycloalkenyl such as a cyclopentenyl group, a cyclohexenyl group or a cyclooctenyl group. Further, the halogen atom contained in each of X and Y may be a fluorine atom, a chlorine atom, a bromine atom or an iodine atom. The aryl group and the aryl moiety contained in each of X and Y may, for example, be a phenyl group, a thienyl group, a furanyl group, a pyridyl group, a naphthyl group, a benzothienyl group, a benzofuranyl group or a quinolinyl group.

Now, preferred embodiments of the compounds of the present invention will be described. In the formula (I), it is preferred that X is a —$CW^1R^1$ group or a —$C(=W^1)W^2R^3$ group and Y is a —$SO_2R^9$ group. Each of $R^1$ and $R^6$ is preferably an alkyl group which may be substituted, an alkenyl group which may be substituted, a cycloalkyl group which may be substituted, a cycloalkenyl group which may be substituted, a phenyl group which may be substituted, a tetrahydronaphthyl group which may be substituted, an indanyl group which may be substituted, a furanyl group which may be substituted or a thienyl group which may be substituted; more preferably an alkyl group, a haloalkyl group, an alkoxycarbonylalkyl group, an alkenyl group, a haloalkenyl group, a cycloalkyl group, a cycloalkyl group substituted with a halogen atom, a phenyl group, a phenyl group substituted with a halogen atom, a phenyl group substituted with an alkyl group or a haloalkyl group, a phenyl group substituted with an alkoxy group or a haloalkoxy group, a tetrahydronaphthyl group, an indanyl group, a furanyl group or a thienyl group. Each of $R^2$ and $R^7$ is preferably an alkoxy group which may be substituted or a phenyl group which may be substituted; more preferably an alkoxy group, a haloalkoxy group, a phenyl group or a phenyl group substituted with a halogen atom. Each of $R^3$, $R^8$ and $R^{10}$ is preferably an alkyl group which may be substituted; more preferably an alkyl group or a haloalkyl group. Each of $R^4$, $R^5$, $R^{11}$ and $R^{12}$ is preferably an alkyl group. $R^9$ is preferably an alkyl group which may be substituted, an alkenyl group which may be substituted, a cycloalkyl group which may be substituted, a cycloalkenyl group which may be substituted or a phenyl group which may be substituted; more preferably an alkyl group, a haloalkyl group, a phenyl group, a phenyl group substituted with a halogen atom, a phenyl group substituted with an alkyl group or a haloalkyl group or a phenyl group substituted with an alkoxy group or a haloalkoxy group.

Preferred compounds among the compounds of the present invention are compounds of the above formula (I) wherein X is an alkoxycarbonylalkylcarbonyl group, an alkenylcarbonyl group, an alkenylcarbonyl group substituted with a thienyl group, a cycloalkylcarbonyl group, an indanylcarbonyl group, a thiophenecarbonyl group, a tetrahydronaphthylcarbonyl group or a benzoyl group which may be substituted with a halogen atom or a haloalkyl group, and Y is an alkylsulfonyl group. Specific compounds include N-(2-ethylsulfonylamino-5-trifluoromethyl-3-pyridyl) cyclohexanecarboxamide, N-(2-methylsulfonylamino-5-trifluoromethyl-3-pyridyl)cyclopentanecarboxamide, N-(2-methylsulfonylamino-5-trifluoromethyl-3-pyridyl)-4-fluorobenzamide, N-(2-methylsulfonylamino-5-trifluoromethyl-3-pyridyl)-5-indancarboxamide, N-(2-methylsulfonylamino-5-trifluoromethyl-3-pyridyl) acetoxyacetamide, N-(2-methylsulfonylamino-5-trifluoromethyl-3-pyridyl)crotonamide, N-(2-methylsulfonylamino-5-trifluoromethyl-3-pyridyl)-2-thiophenecarboxamide, N-(2-methylsulfonylamino-5-trifluoromethyl-3-pyridyl)-3-trifluoromethylbenzamide, N-(2-ethylsulfonylamino-5-trifluoromethyl-3-pyridyl)-3-fluorobenzamide, N-(2-methylsulfonylamino-5-trifluoromethyl-3-pyridyl)-6-(1,2,3,4-tetrahydronaphthalene)carboxamide, N-(2-ethylsulfonylamino-5-trifluoromethyl-3-pyridyl) crotonamide and N-(2-methylsulfonylamino-5-trifluoromethyl-3-pyridyl)-3-(2-thienyl)acrylamide, and their salts.

More preferred compounds may be compounds of the above formula (I) wherein X is a cycloalkylcarbonyl group, an alkenylcarbonyl group, a thiophenecarbonyl group or a benzoyl group which may be substituted with a halogen atom, and Y is an alkylsulfonyl group. Specific compounds include N-(2-ethylsulfonylamino-5-trifluoromethyl-3-pyridyl)cyclohexanecarboxamide, N-(2-methylsulfonylamino-5-trifluoromethyl-3-pyridyl) crotonamide, N-(2-methylsulfonylamino-5-trifluoromethyl-3-pyridyl)-2-thiophenecarboxamide, N-(2-methylsulfonylamino-5-trifluoromethyl-3-pyridyl) cyclopentanecarboxamide and N-(2-methylsulfonylamino-5-trifluoromethyl-3-pyridyl)-4-fluorobenzamide, and their salts.

The compounds represented by the formula (I) may form a salt when Y is a —$SO_2R^9$ group (wherein $R^9$ is as defined above). Such a salt may be any pharmaceutically acceptable salt, for example, an alkali metal salt such as a potassium salt or a sodium salt, an alkaline earth metal salt such as a calcium salt, or an organic amine salt such as a triethanolamine salt or a tris(hydroxymethyl)aminomethane salt. Such a salt may have crystal water.

The compounds represented by the formula (I) can be prepared, for example, by a process as disclosed in Japanese Patent No. 2762323. Further, these compounds have geometrical isomers depending upon the type of their substituents, and the present invention includes isomers (cis-forms and trans-forms) and isomer mixtures.

The compounds represented by the above formula (I) of the present invention are useful as an active ingredient for a therapeutic agent for pulmonary insufficiency represented by acute respiratory distress syndrome (ARDS) and chronic obstructive pulmonary disease (COPD). It is particularly useful as an active ingredient for a therapeutic agent particularly for ARDS among various pulmonary insufficiencies. They are expected to be more effective by combination with another drug.

To administer the compound of the present invention as an active ingredient for a therapeutic agent for acute pulmonary impairment, it is formulated alone or together with a pharmaceutically acceptable carrier into a drug composition suitable for peroral or parenteral administration, such as a tablet, a powder, a capsule, a granule, an injection drug, an ointment, an inhalant, an enema or a suppository, and it is administered in the form of such a drug formulation.

As a drug formulation suitable for peroral administration, a solid composition such as a tablet, a capsule, a powder, a granule or a troach; or a liquid composition such as a syrup suspension, may, for example, be mentioned. The solid composition such as a tablet, a capsule, a powder, a granule or a troach may contain a binder such as fine crystalline cellulose, gum arabic, tragacanth gum, gelatine or polyvinyl pyrrolidone; an excipient such as starch, lactose or carboxymethyl cellulose; a disintegrator such as arginic acid, corn starch or carboxymethyl cellulose; a lubricant such as magnesium stearate, light silicic anhydride or colloidal silicon dioxide; a sweetener such as sucrose; or a flavoring agent such as peppermint or methyl salicylate. The liquid composition such as a syrup or a suspension may contain sorbitol, gelatine, methyl cellulose, carboxymethyl cellulose, a vegetable oil such as a peanut oil, an emulsifier such as lecithin as well as a sweetener, a preservative, a colorant or a flavoring agent, as the case requires. Such a composition may be provided in the form of a dried formulation. These formulations preferably contain from 1 to 95 wt % of the active ingredient compound.

A drug formulation suitable for parenteral administration may, for example, be an injection drug. The injection drug may be prepared by dissolving the compound in the form of a salt in usual water for injection, or may be formulated into a formulation suitable for injection such as a suspension or an emulsion (in a mixture with a medically acceptable oil or liquid). In such a case, it may contain benzyl alcohol as an antibacterial agent, ascorbic acid as an antioxidant, a medically acceptable buffer solution or a reagent for adjusting the osmotic pressure. Such an injection drug preferably contains from 0.1 to 8 wt % of the active ingredient compound.

A drug formulation suitable for topical or per rectal administration may, for example, be an inhalant, an ointment, an enema or a suppository. The inhalant may be formulated by dissolving the compound of the present invention alone or together with a medically acceptable inert carrier in an aerosol or nebulizer solution, or may be administered to the respiratory airway in the form of fine powder for inhalation. In the case of fine powder for inhalation, the particle size is usually not more than $50\mu$, preferably not more than $10\mu$. Such an inhalant may be used, if necessary, in combination with other antiasthematic agent or bronchodilator.

An ointment may be prepared by a conventional method by an addition of e.g. a commonly employed base. The ointment preferably contains from 0.1 to 30 wt % of the active ingredient compound.

A suppository may contain a carrier for formulation which is well known in this field, such as polyethylene glycol, lanolin, cacao butter or fatty acid triglyceride. The suppository preferably contains from 1 to 95 wt % of the active ingredient compound.

The above drug compositions suitable for peroral, parenteral, topical or per rectal administration, may be formulated by known methods so that after administration to a patient, the active ingredient will be rapidly discharged, gradually discharged or belatedly discharged.

Needless to say, the dose of the compound of the present invention varies depending upon the type of the compound, the administration method, the condition of the patient or the animal to be treated, and the optimum dose and the number of administration under a specific condition must be determined by the judgment of a competent doctor. Usually, however, a daily dose to an adult is from about 0.1 mg to about 10 g, preferably from about 1 mg to about 1 g. In the case of the above inhalation method, the dose of the compound of the present invention is preferably from about 0.01 mg to about 1 g per administration.

Now, specific Formulation Examples of the therapeutic or preventive agent for pulmonary insufficiency of the present invention will be given. However, the formulation of the present invention is not limited thereto.

Formulation Example 1 (Tablet)

| | |
|---|---|
| (1) Active ingredient | 20 mg |
| (2) Lactose | 150 mg |
| (3) Starch | 30 mg |
| (4) Magnesium stearate | 6 mg |

The above composition is tabletted so that the components (1) to (4) constitute one tablet.

Formulation Example 2 (Powder, Subtilized Granule or Granule)

| | |
|---|---|
| (1) Active ingredient | 20 mg |
| (2) Sugar ester (DK ester F-160, tradename, manufactured by DAI-ICHI KOGYO SEIYAKU CO., LTD.) | 180 mg |
| (3) Surfactant (DECA-GREEN 1-L, tradename, manufactured by Nikko Chemicals Co., Ltd.) | 15 mg |
| (4) Light silicic anhydride | 25 mg |

The above components (1) to (4) are mixed and formed into a powder, or subtilized granule or granule by granulation. Such a powder, subtilized granule or granule may be sealed in a capsule to obtain a capsule drug.

Formulation Example 3 (Hard Gelatine Capsule Drug)

| | |
|---|---|
| (1) Active ingredient | 25 mg |
| (2) Starch | 200 mg |
| (3) Magnesium stearate | 10 mg |

The above components (1) to (3) are packed in one hard gelatine capsule to obtain a hard gelatine capsule drug.

Formulation Example 4 (Injection Drug)

| | |
|---|---|
| (1) Active ingredient | 1 mg |
| (2) Glucose | 10 mg |
| (3) Tris(hydroxymethyl)aminomethane | 2.16 mg |

A tris buffer containing the components (1) to (3) is freeze-dried to prepare an injection drug.

Formulation Example 5 (Ointment for External Skin Application)

| (1) Active ingredient | 0.5 g |
|---|---|
| (2) White vaseline | 25 g |
| (3) Stearyl alcohol | 22 g |
| (4) Propylene glycol | 12 g |
| (5) Sodium lauryl sulfate | 1.5 g |
| (6) Ethyl parahydroxybenzoate | 0.025 g |
| (7) Propyl parahydroxybenzoate | 0.015 g |
| (8) Purified water | 100 g |

The components (1) to (8) are formulated into an ointment for external skin application by a usual method for preparation of an ointment.

Formulation Example 6 (Enema Formulation)

| (1) Active ingredient | 50 mg |
|---|---|
| (2) Macrogol 400 | 2 g |
| (3) Dipotassium phosphate | 141 mg |
| (4) Potassium dihydrogenphosphate | 44 mg |
| (5) Methyl parahydroxybenzoate | 20 mg |
| (6) Purified water | 50 g |

The active ingredient and methyl parahydroxybenzoate are added to Macrogol 400, followed by stirring to obtain a mixture, to which one obtained by adding dipotassium phosphate and potassium dihydrogenphosphate to the purified water is gradually added to prepare an enema formulation.

Formulation Example 7 (Supository)

| (1) Active ingredient | 50 g |
|---|---|
| (2) Higher fatty acid glyceride | 1,650 mg |

The component (1) is dispersed or dissolved in (2), and packed and sealed in a plastic container having a size appropriate as a suppository, followed by cooling for solidification to prepare a suppository.

Formulation Example 8 (Rectum Remaining Suppository, Controlled Release Suppository)

| (1) Active ingredient | 1 g |
|---|---|
| (2) Witepsol W35 | 19 g |

The component (1) is admixed with preliminarily heated and dissolved (2), and the admixture is packed and sealed in a plastic container having a size appropriate as a suppository, followed by cooling for solidification to prepare a suppository.

EXAMPLES

Test Example 1

Therapeutic Effect on Lipopolysaccharide (LPS) Induced Rat ARDS Model

The therapeutic effect of N-(2-ethylsulfonylamino-5-trifluoromethyl-3-pyridyl)cyclohexanecarboxamide sodium salt hydrate (hereinafter referred to as compound 1) on LPS induced rat ARDS model was examined.

(1) Formulation of Compound 1

The compound 1 was used as a drug formulation. The formulation composition (content per one vial) was as follows.

| (a) Compound 1 (as anhydride) | 100 mg |
|---|---|
| (b) D-mannitol (manufactured by KYOWA HAKKO KOGYO CO., LTD.) | 100 mg |
| (c) Tris(hydroxymethyl)aminomethane (manufactured by JUNSEI CHEMICAL) | 21.6 mg |
| (d) Hydrochloric acid (manufactured by SANKYO KAGAKU) | optimum amount |
| (e) Sodium hydroxide (manufactured by Nippon Rika) | optimum amount |
| (f) Distilled water | 10 ml |
| pH 8.7 ± 0.5 | |

(2) Induction of ARDS

To Crj: CD(SD)IGS male rats (7 weeks old) (Charles River Japan Inc.), LPS (derived from Salmonella enteritidis; L6011, Lot. 27H4127, manufactured by Sigma) diluted with a phosphate buffer solution (PBS) was administered by spraying it on the trachea in a dose of 8 mg/kg (0.5 ml/rat) by means of an atomizer (endotracheal liquid atomizing apparatus 1A-1B, manufactured by Penn Century) to induce ARDS. For normal group rats, PBS was similarly sprayed.

(3) Administration of Drug

A drug formulation of the compound 1 diluted with 5% glucose was subcutaneously administered continuously in a dose of 0.3 mg/kg/hr as calculated as anhydride of the compound 1 by means of an osmotic pump from immediately after the induction to the time of autopsy (24 hours after). To non-treated group rats, 5% glucose used as the solvent was administered similarly.

(4) Judgment of Effect

24 Hours after the administration of LPS, measurement of the body weight and the lung wet weight, biochemical examination of blood and pathological and histopathological examinations were carried out with respect to every surviving rats.

No death was confirmed 24 hours after the LPS administration, and thus various examinations were carried out with respect to every rat. The results of the pathological examination and histopathological examination are shown in Tables 1 and 2. Here, the pathological score was obtained by evaluating each rat in five stages of −(no significant lesion), ±(slight), +(mild), ++(moderate) and +++(marked), and allotting 0, 0.5, 1, 2 and 3 points, respectively, to obtain the average of each group.

TABLE 1

Autopsy findings of lung (average of score in each group)

| Group | Normal group | | Non-treated group | | Compound 1 group | |
|---|---|---|---|---|---|---|
| Dosage (mg/kg/hr × 24 hr) | 0 | | 0 | | 0.3 | |
| | Mean | SD | Mean | SD | Mean | SD |
| Edema | 0.0 | 0.0 | 0.4 | 0.8 | 0.1 | 0.3 |
| Hemorrhage | 0.4 | 0.2 | 1.0 | 0.6* | 0.5 | 0.5 |
| Congestion | 0.4 | 0.2 | 2.8 | 0.6** | 2.2 | 0.4# |

SD: standard deviation
*P < 0.01,
**P < 0.001 (normal group vs. non-treated group, Wilcoxon 2-sample test)
P < 0.01 (non-treated group vs. compound 1 group, Wilcoxon 2-sample test)

TABLE 2

Histopathological findings of alveoli (average of score in each group)

| Group | Normal group | | Non-treated group | | Compound 1 group | |
|---|---|---|---|---|---|---|
| Dose (mg/kg/hr × 24 hr) | 0 | | 0 | | 0.3 | |
| | Mean | SD | Mean | SD | Mean | SD |
| Collapse of alveolar wall | 0.0 | 0.0 | 2.7 | 0.9# | 1.2 | 0.8* |
| Hemorrhage in alveoli | 0.0 | 0.0 | 2.7 | 0.9# | 1.5 | 1.0* |
| Alveolar edema | 0.2 | 0.4 | 2.8 | 0.6# | 1.4 | 1.0* |
| Fibrin deposit in alveoli | 0.0 | 0.0 | 2.8 | 0.6# | 1.5 | 1.0* |

SD: standard deviation
P < 0.001 (normal group vs. non-treated group, Wilcoxon 2-sample test)
*P < 0.01 (non-treated group vs. compound 1 group, Wilcoxon 2-sample test)

In the non-treated group (5% glucose administered group), exudative changes and regressive changes in the lung and the trachea with an increase of the lung wet weight were confirmed. Further, from the increase in a blood erythrocyte examination item, hemoconcentration was also confirmed, and general pathological symptoms of ARDS were confirmed. On the other hand, in the compound 1 administered group, collapse of the alveolar wall, alveolar edema and hemorrhage, and fibrin deposit in the alveoli which were severe changes in this test system were reduced, and a remarkable inhibition effect against ARDS pathological progress was confirmed.

Test Example 2

Therapeutic Effect on Cigarette Smoke Inhalation Rat Chronic Obstructive Pulmonary Disease (COPD) Model The therapeutic effect of N-(2-ethylsulfonylamino-5-trifluoromethyl-3-pyridyl)cyclohexanecarboxamide sodium salt hydrate (compound 1) on cigarette smoke inhalation rat COPD model can be confirmed by the following method.
(1) Induction of COPD
Using Crj: CD(SD)IGS male rats (6 weeks old) (Charles River Japan Inc.), their head is exposed to the smoke of ten commercially available non-filter cigarettes per day, five days in a week, over two months (8 weeks) by means of a cigarette smoke exposure apparatus (INH06-CIGR01, manufactured by MIPS K.K.). Normal group rats are similarly exposed to fresh air.
(2) Administration of Drug
To compound 1 group rats, a drug formulation of the compound 1 diluted with 5% glucose (used in Test Example 1) is subcutaneously administered continuously in an amount of 0.03 mg/kg/hr as calculated as anhydride of the compound 1 by means of an osmotic pump from the time of the induction to the time of autopsy. To non-treated group rats, 5% glucose used as the solvent is administered similarly.
(3) Judgment of Effect
After completion of the exposure, measurement of the trachea resistance, and pathological and histopathological examinations are carried out with respect to every surviving rat.
The inhibition effect on COPD can be confirmed when it can be confirmed that changes confirmed in the non-treated group (5% glucose administered group) are reduced in the compound 1 group.

What is claimed is:

1. A method for preventing or treating pulmonary insufficiency, comprising administering to a subject in need thereof an effective amount of a diaminotrifluoromethylpyridine compound or its salt, wherein said compound is represented by formula (I):

$$F_3C \diagdown \diagup NHX \atop N \diagdown NHY \qquad (I)$$

wherein
X is a —$CW^1R^1$ group, a —$COCOR^2$ group, a —$CW^1NHCOR^2$ group, a —$C(=W^1)W^2R^3$ group or a —$CW^1N(R^4)R^5$ group;

Y is an alkyl group, a —$CW^3R^6$ group, a —COCOR group, a —$NHCOR^7$ group, a —$C(=W^3)W^4R^8$ group, a —$(NH)_mSO_2R^9$ group, a —$(NH)_mSO_2OR^{10}$ group or a —$(NH)_mSO_2N(R^{11})R^{12}$ group;

wherein each of $R^1$, $R^6$ and $R^9$, which are independent of one another, is a chain hydrocarbon group which may be substituted, a monocyclic hydrocarbon group which may be substituted, a polycyclic hydrocarbon group which may be substituted, a monocyclic heterocycle group which may be substituted or a polycyclic heterocycle group which may be substituted;

wherein each of $R^2$ and $R^7$, which are independent of each other, is an alkyl group which may be substituted, an alkoxy group which may be substituted, a phenyl group which may be substituted or a phenoxy group which may be substituted;

wherein each of $R^3$, $R^8$ and $R^{10}$, which are independent of one another, is an alkyl group which may be substituted, an alkenyl group which may be substituted, an alkynyl group which may be substituted, a cycloalkyl group which may be substituted, a phenyl group which may be substituted or a benzyl group which may be substituted;

wherein each of $R^4$, $R^5$, $R^{11}$ and $R^{12}$, which are independent of one another, is an alkyl group which may be substituted; each of $W^1$, $W^2$, $W^3$ and $W^4$ which are independent of one another, is an oxygen atom or a sulfur atom; and wherein m is 0 or 1;

wherein said compound of formula (I) is not a compound where one of X and Y is a —COCF$_2$X$^1$ group (wherein X$^1$ is a hydrogen atom, a halogen atom, an alkyl group or a haloalkyl group), and the other is a —COCF$_2$X$^2$ group (wherein X$^2$ is a hydrogen atom, a halogen atom, an alkyl group, a haloalkyl group or an alkylcarbonyl group), a —COOX$^3$ group (wherein X$^3$ is an alkyl group which may be substituted or a phenyl group which may be substituted) or a —COX$^4$ group (wherein X$^4$ is an alkyl group, a haloalkyl group, an alkenyl group, an alkynyl group, a phenyl group which may be substituted, a furanyl group or a naphthyl group).

2. The method of claim 1, wherein

X is a —CW$^1$R$^1$ group or a —C(=W$^1$)W$^2$R$^3$ group and

Y is a —SO$_2$R$^9$ group.

3. The method of claim 1, wherein

X is a —CW$^1$R$^1$ group or a —C(=W$^1$)W$^2$R$^3$ group,

R$^1$ is an alkyl group which may be substituted, an alkenyl group which may be substituted, a cycloalkyl group which may be substituted, a cycloalkenyl group which may be substituted, a phenyl group which may be substituted, a tetrahydronaphthyl group which may be substituted, an indanyl group which may be substituted, a furanyl group which may be substituted or a thienyl group which may be substituted, R$^3$ is an alkyl group which may be substituted, Y is a —SO$_2$R$^9$ group, and R$^9$ is an alkyl group which may be substituted, an alkenyl group which may be substituted, a cycloalkyl group which may be substituted, a cycloalkenyl group which may be substituted or a phenyl group which may be substituted.

4. The method of claim 1, wherein

X is a —CW$^1$R$^1$ group or a —C(=W$^1$)W$^2$R$^3$ group,

R$^1$ is an alkyl group, a haloalkyl group, an alkoxycarbonyl alkyl group, an alkenyl group, a haloalkenyl group, an alkenyl group substituted with a thienyl group, a cycloalkyl group, a cycloalkyl group substituted with a halogen atom, a phenyl group, a phenyl group substituted with a halogen atom, a phenyl group substituted with an alkyl group or a haloalkyl group, a phenyl group substituted with an alkoxy group or a haloalkoxy group, a tetrahydronaphthyl group, an indanyl group, a furanyl group or a thienyl group, R$^3$ is an alkyl group or a haloalkyl group, Y is a —SO$_2$R$^9$ group, and R$^9$ is an alkyl group, a haloalkyl group, a phenyl group, a phenyl group substituted with a halogen atom, a phenyl group substituted with an alkyl group or a haloalkyl group, or a phenyl group substituted with an alkoxy group or a haloalkoxy group.

5. The method of claim 1, wherein

X is an alkoxycarbonyl alkylcarbonyl group, an alkenylcarbonyl group, an alkenylcarbonyl group substituted with a thienyl group, a cycloalkylcarbonyl group, an indanylcarbonyl group, a thiophenecarbonyl group, a tetrahydronaphthylcarbonyl group or a benzoyl group which may be substituted with a halogen atom or a haloalkyl group, and Y is an alkylsulfonyl group.

6. The method of claim 1, wherein

X is a cycloalkylcarbonyl group, an alkenylcarbonyl group, a thiophenecarbonyl group or a benzoyl group which may be substituted with halogen, and Y is an alkylsulfonyl group.

7. The method of claim 1, wherein the diaminotrifluoromethylpyridine compound is selected from the group consisting of N-(2-ethylsulfonylamino-5-trifluoromethyl-3-pyridyl)cyclohexanecarboxamide, N-(2-methylsulfonylamino-5-trifluoromethyl-3-pyridyl)crotonamide, N-(2-methylsulfonylamino-5-trifluoromethyl-3-pyridyl)-2-thiophenecarboxamide, N-(2-methylsulfonylamino-5-trifluoromethyl-3-pyridyl)cyclopentanecarboxamide and N-(2-methylsulfonylamino-5-trifluoromethyl-3-pyridyl)-4-fluorobenzamide.

8. The method of claim 1, wherein the diaminotrifluoromethylpyridine compound is N-(2'-ethylsulfonylamino-5-trifluoromethyl-3-pyridyl)cyclohexanecarboxamide.

9. The method of claim 1 that is a method for preventing pulmonary insufficiency.

10. The method of claim 1 that is a method for treating pulmonary insufficiency.

11. The method of claim 1, wherein said pulmonary insufficiency is a disease selected from the group consisting of acute respiratory distress syndrome and chronic obstructive pulmonary disease.

12. The method of claim 1, further comprising administering at least one other drug, or therapeutic agent.

13. The method of claim 1, comprising administering an alkaline metal salt, an alkaline earth metal salt or an organic amine salt of said compound.

14. The method of claim 1, comprising administering said compound perorally.

15. The method of claim 14, wherein said compound is formulated in a manner to be rapidly discharged, be gradually discharged, or be belatedly discharged once administered to a subject.

16. The method of claim 1, comprising administering said compound in the form of a tablet, capsule, powder, granule, troche, liquid, suspension, emulsion, ointment, suppository, enema, or syrup.

17. The method of claim 1, comprising administering said compound parenterally.

18. The method of claim 1, comprising administering said compound topically or by rectal administration.

19. The method of claim 1, comprising administering said compound via the respiratory airway or by inhalation.

20. The method of claim 1, comprising administering to a daily dose ranging from 0.1 mg to about 10 g of said diaminotrifluoromethylpyridine compound or its salt.

21. The method of claim 1, comprising administering a daily dose ranging from 1 mg to about 1 g of said diaminotrifluoromethylpyridine compound or its salt.

22. The method of claim 1, further comprising at least one antibacterial agent or antioxidant.

23. The method of claim 1, further comprising a medically acceptable buffer solution, a medically acceptable reagent, or a medically acceptable inert carrier.

* * * * *